(12) United States Patent
Nejat

(10) Patent No.: US 8,011,057 B2
(45) Date of Patent: Sep. 6, 2011

(54) RETRACTABLE INTERPROXIMAL BRUSH

(76) Inventor: Richard Nejat, New York, NY (US)

( * ) Notice: Subject to any disclaimer, the term of this patent is extended or adjusted under 35 U.S.C. 154(b) by 394 days.

(21) Appl. No.: 11/881,642

(22) Filed: Jul. 26, 2007

(65) Prior Publication Data

US 2009/0029323 A1    Jan. 29, 2009

(51) Int. Cl.
- A61C 17/22 (2006.01)
- A61C 17/32 (2006.01)
- A46B 9/04 (2006.01)

(52) U.S. Cl. .......... 15/167.1; 15/22.1; 15/22.2; 433/216

(58) Field of Classification Search .............. 15/167.1, 15/184, 172; 433/102, 164, 125
See application file for complete search history.

(56) References Cited

U.S. PATENT DOCUMENTS

| | | | |
|---|---|---|---|
| 4,780,923 A | 11/1988 | Schultheiss | |
| 4,787,847 A | 11/1988 | Martin | |
| 4,977,909 A * | 12/1990 | Chou | 132/123 |
| 5,029,358 A | 7/1991 | Zimmerman | |
| 5,123,841 A | 6/1992 | Millner | |
| 5,263,218 A | 11/1993 | Giuliani | |
| 5,350,248 A * | 9/1994 | Chen | 401/195 |
| 5,490,529 A | 2/1996 | Fitjer | |
| 5,573,020 A * | 11/1996 | Robinson | 132/322 |
| 5,775,346 A | 7/1998 | Szyszkowski | |
| 5,855,216 A * | 1/1999 | Robinson | 132/322 |
| 5,927,300 A * | 7/1999 | Boland et al. | 132/322 |
| 6,050,818 A * | 4/2000 | Boland et al. | 433/118 |
| 6,349,442 B1 * | 2/2002 | Cohen et al. | 15/22.1 |
| 6,821,119 B2 * | 11/2004 | Shortt et al. | 433/118 |
| 7,147,470 B2 * | 12/2006 | Lesage | 433/141 |
| 2001/0054211 A1 | 12/2001 | Cabedo-Deslierres | |
| 2003/0079304 A1 * | 5/2003 | Dworzan | 15/22.1 |
| 2003/0115693 A1 * | 6/2003 | Grez et al. | 15/22.1 |

(Continued)

FOREIGN PATENT DOCUMENTS

JP    2003260071 A  *  9/2003

(Continued)

OTHER PUBLICATIONS

Oral-B package, Interdental Handle/Clip (1 page) (undated).

Primary Examiner — Monica S Carter
Assistant Examiner — Stephanie Newton
(74) Attorney, Agent, or Firm — Brenda Pomerance

(57) ABSTRACT

There are provided a device and a method for cleaning teeth. The device comprises a brush, a shaft connected to the brush, a neck surrounding the shaft along a substantial portion of the length of the shaft, and a controller coupled to the shaft at the end of the shaft opposite the brush, the controller being mounted at the base of the neck so as to be movable between a first position that extends the brush away from the neck, and a second position that retracts the brush towards the neck. The method comprises inserting, between adjacent teeth, a device having a brush, a controller and a handle, the controller for effecting movement of the brush in a direction generally perpendicular to the handle, and keeping the handle generally stationary while moving the controller up and down to move the brush along front-to-back and back-to-front paths between the adjacent teeth. Moving the controller may occur via pressure from a user's finger, or via force from a motor in the device. In some cases, the method includes vibrating the brush while it is moved along the front-to-back and back-to-front paths between the adjacent teeth.

11 Claims, 7 Drawing Sheets

U.S. PATENT DOCUMENTS

| | | |
|---|---|---|
| 2003/0224320 A1 | 12/2003 | Kandelman |
| 2004/0197735 A1 | 10/2004 | Lesage |
| 2005/0037316 A1* | 2/2005 | Sholder .......................... 433/119 |
| 2006/0254010 A1 | 11/2006 | Wagner |
| 2008/0115799 A1* | 5/2008 | Weiss ............................ 132/328 |

FOREIGN PATENT DOCUMENTS

| | | |
|---|---|---|
| JP | 2004-313455 | 11/2004 |
| WO | WO 03 086 231 | 11/2003 |

* cited by examiner

RETRACTABLE INTERPROXIMAL BRUSH

BACKGROUND OF THE INVENTION

The present invention relates an appliance for cleaning teeth, and more particularly, is directed to a brush suited for cleaning the interproximal areas of teeth.

Keeping one's teeth clean is important not only for dental health, but also for cardiovascular health. Known toothbrushes are aggressive in plaque removal on the easily accessed buccal (cheek) and lingual (tongue) surfaces, but are less effective, or wholly ineffective, on interproximal (between adjacent teeth) surfaces. Aggressive cleaning on one or two surfaces of teeth may be of marginal benefit if the remaining surfaces receive less effective cleaning, since the plaque remains in the mouth to inflict periodontal disease (gumdisease and dental caries (cavities).

Various devices have been proposed for improved interproximal cleaning. U.S. Pat. No. 4,780,923 (Schultheiss) discloses a handle with a bristle brush at a small angle to the handle. The device is used by inserting the bristles between the teeth and moving the handle towards and away from the teeth to cause the bristles to dislodge plaque from the interproximal surfaces. U.S. Patent Application Publication No. 2005/0037316 (Sholder) (abandoned) discloses a molded tip inserted into an arm adapted to be coupled to a base that generates sonic energy. The molded tip is of generally conical shape and includes elastomeric flat-faced flanges extending perpendicularly outwards from the base to the tip in a staggered pattern.

With known devices, often the brush bends when fitted in between the teeth. In addition, since interproximal embrasures (the spaces between teeth) vary from 0.1 to 6 mm or larger, a successful interproximal device must be able to work in a range of aperture sizes.

Accordingly, there is room for an improved interproximal cleaning device.

SUMMARY OF THE INVENTION

In accordance with an aspect of this invention, there are provided a device and a method for cleaning teeth.

The device comprises a brush, a shaft connected to the brush, a neck surrounding the shaft along a substantial portion of the length of the shaft, and a controller coupled to the shaft at the end of the shaft opposite the brush, the controller being mounted at the base of the neck so as to be movable between a first position that extends the brush away from the neck, and a second position that retracts the brush towards the neck.

In some cases, the brush has nylon bristles attached to a shaft. The shaft is preferably formed of a material that returns to its original shape after being deformed, such as nickel-titanium. The controller may have at least one surface for manual operation thereof. A tip may be attached to the neck, to surround and guide the brush when the brush is extended. An elbow having an adjustable curvature may be connected between the tip and the neck.

In some cases, the device also has a motor for moving the shaft so that the brush extends and retracts, or a motor for vibrating the shaft and brush bristles.

The method comprises inserting, between adjacent teeth, a device having a brush, a controller and a handle, the controller for effecting movement of the brush in a direction generally perpendicular to the handle, and keeping the handle generally stationary while moving the controller up and down to move the brush along front-to-back and back-to-front paths between the adjacent teeth. Moving the controller may occur via pressure from a user's finger, or via force from a motor in the device. In some cases, the method includes vibrating the brush while it is moved along the front-to-back and back-to-front paths between the adjacent teeth.

It is not intended that the invention be summarized here in its entirety. Rather, further features, aspects and advantages of the invention are set forth in or are apparent from the following description and drawings.

DETAILED DESCRIPTION

Generally, one of the most difficult areas in the mouth to clean is the interproximal area of the posterior (back) teeth. As used herein and in the claims, cleaning refers to removing food and/or plaque from the surface of at least one tooth. The difficulty is due to the narrowing of the mouth opening towards the throat, and reduced room to maneuver a device inserted in the mouth. The present interproximal device mitigates the maneuvering difficulty by translating movement along its handle to movement of the generally perpendicular brush on its tip. Thus, the interproximal area can be brushed by extending and retracting the brush; the thumb/finger action for moving the retractor often being an easier movement to accomplish than moving the brush directly. Further, the present configuration makes it easier to effect cleaning on both the front-to-back and back-to-front paths of the brush; in contrast, prior art devices generally effect the majority of their cleaning on the front-to-back path. These advantages are also present when using the device on the anterior (front) teeth.

Other difficult areas to clean are under a dental implant bridge, under a tooth bridge, and around orthodontic braces; the present device is also effective in these areas.

Additionally, some types of manual disabilities make it difficult for the disabled person to use conventional interproximal cleaners; the present device configuration is easier for these disabled persons to use due to control of the spring loaded interproximal tip or motorized control switch located on the handle.

Figure 1:
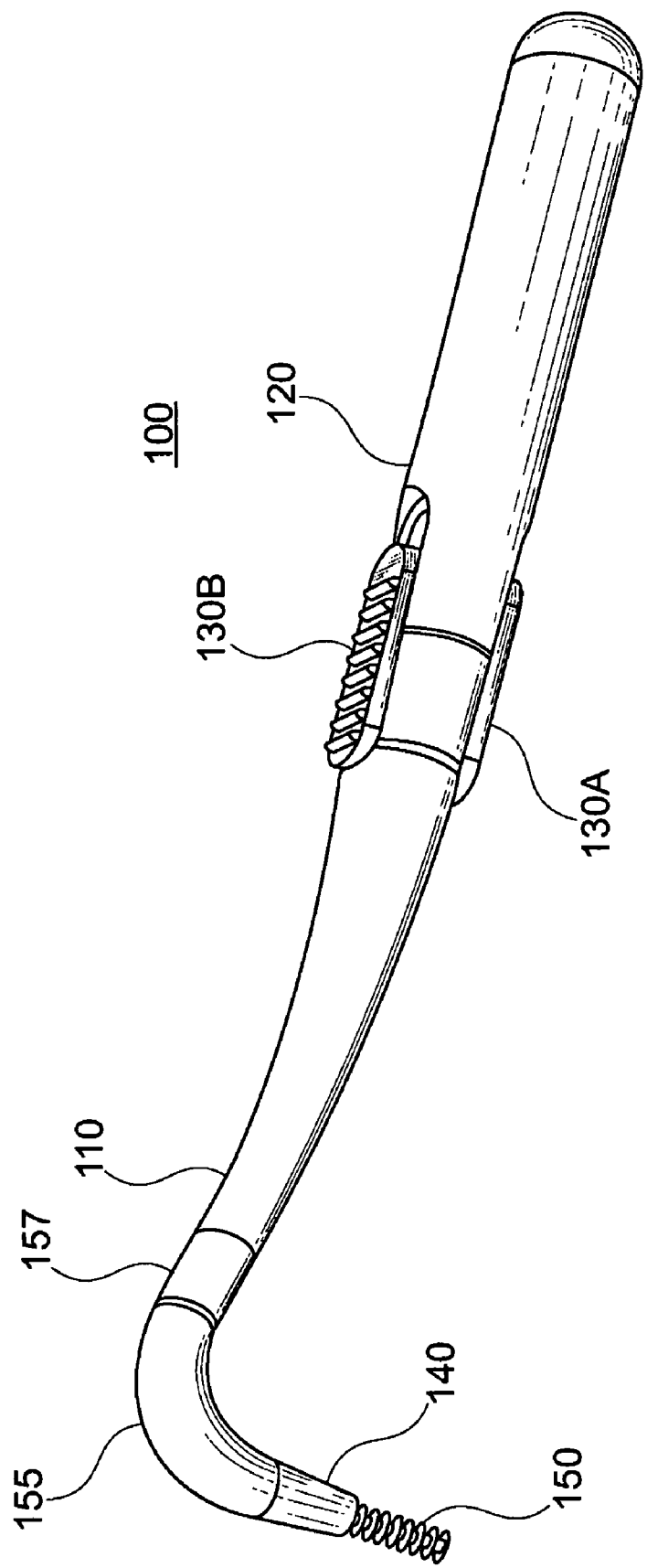
FIG. 1 is a three-dimensional view of interproximal cleaning device 100.

Referring now to the drawings, and in particular to FIG. 1, there is illustrated interproximal device 100 having brush 150, tip 140, elbow 155, coupler 157, neck 110, controller 130 having surfaces 130A and 130B, and handle 120. The apparatus illustrated in FIG. 1 is adapted for retracting and extending brush 150 by moving controller 130, thereby enabling improved interproximal cleaning.

Figure 2:
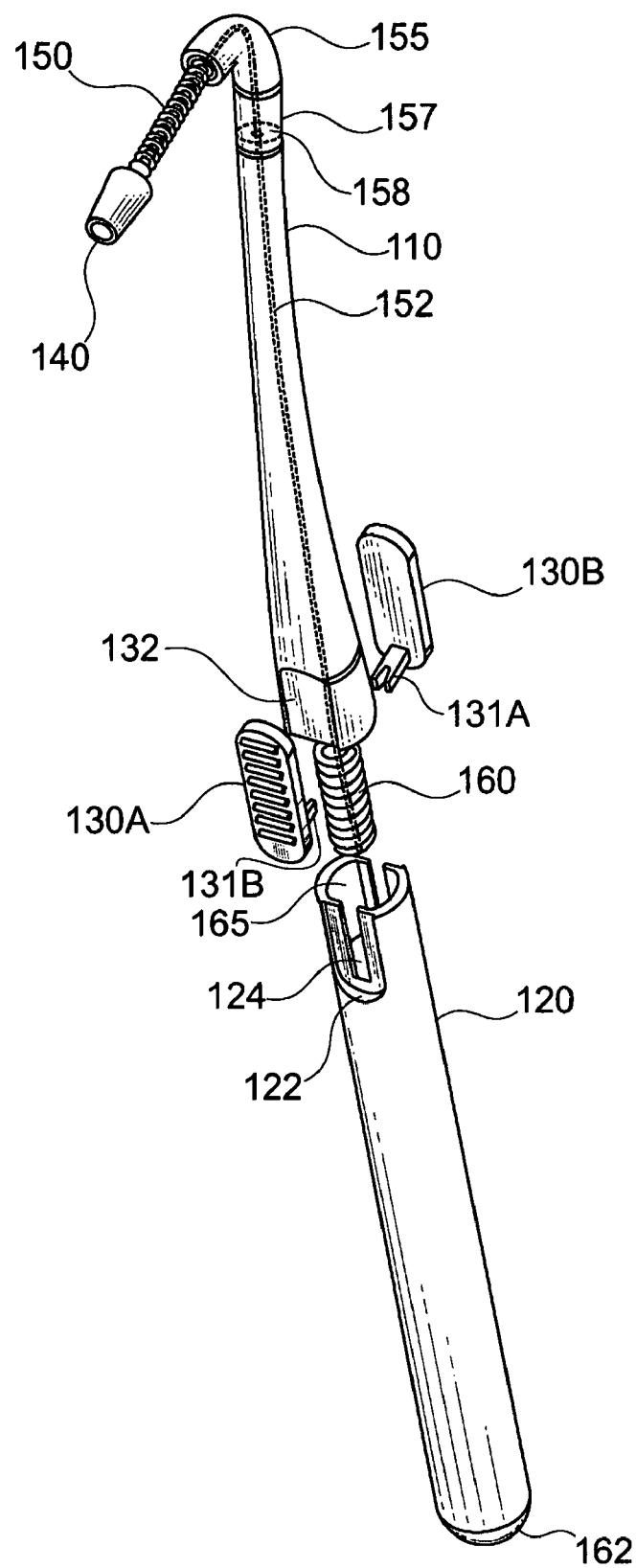
FIG. 2 is a break-apart view of interproximal cleaning device 100.

FIG. 2 shows a break-apart view of device 100, including the aforementioned parts and shaft 152, membrane 158, spring or coil 160, cavity 165, U-shaped groove 122, slot 124, prong 131A, prong receiver 131B, landing pad 132, and base 162.

The housing of device 100 comprises tip 140 connected, such as by being screwed, to the outer edge of elbow 155 which is screwed into coupler 157 that in turn is connected to neck 110 that is adjacent to handle 120. In some embodiments, device 100 is disposable and/or proportionally smaller to be in a "travel size" configuration.

For consumer use, the housing of device 100 is cleaned by placing device 100 under running water. For consumer use, tip 140 and brush 150 are replaceable. For consumer use, the bottom of neck 110 may be glued to the top of handle 120.

For professional use, device 100 is sterilized in an autoclave between uses. For professional embodiments, elbow 155, coupler 157 and neck 110 have small ventilation holes (not shown) that facilitate penetration of steam from the autoclave (steam sterilizer) or other suitable sterilizer. For professional use, tip 140, brush 150, shaft 152 and coil 160 are replaceable or disposable. For professional use, the bottom of neck 110 has flanges (not shown) that enable a removable force-fit into the top of handle 120.

Tip 140 is formed of rubber or similar material in a generally conical tapered shape, and is intended to be replaced from time to time as it may wear with use. When brush 150 is retracted, its end is inside tip 140; whereas when brush 150 is extended, its end extends beyond tip 140. As discussed below, the amount of extension is controllable by the user. Tip 140 screws into elbow 155 (the threaded portions of tip 140 and elbow 155 are not shown). In other embodiments, the inner circumference of tip 140 is slightly smaller than the outer circumference of elbow 155, and tip 140 is pressed into place surrounding the top edge of elbow 155. In other embodiments where tip 140 is not replaceable, it is glued to elbow 155, or formed as an extension to elbow 155. Tip 140 serves to assist in positioning brush 150, to clean, massage and stimulate the gums of the user which increases blood flow and improves the user's immune system's response to bacteria, and to clean brush 150 as brush 150 is retracted due to a squeegee action on the bristles of brush 150.

Positioning brush 150 is important. With prior interproximal devices, the brush often quickly bends with use so that it no longer inserts perpendicularly between teeth, making it difficult to use in the mouth, more susceptible to breakage, and reducing the lifetime of the device. Tip 140 and the retractable nature of brush 150 mitigates these problems in device 100.

Elbow 155, coupler 157, neck 110 and handle 120 are formed of plastic, such as cellulose acetate propionate, nylon, polyethylene, polypropylene, polycarbonate, polyethylene terephthalate or the like. In other embodiments, these parts are formed of metal. In some embodiments, the curvature of elbow 155 can be adjusted by bending elbow 155, to achieve a more comfortable wrist position for the user. In some embodiments, elbow 155 has small ventilation holes so that the bristles of brush 150 can "breathe" and dry after use; these ventilation holes are also helpful when elbow 155 is intended to be cleaned in an autoclave.

Neck 110 serves to support shaft 152. Neck 110 has guides to create a channel for shaft 152. In other embodiments, neck 110 has a thin channel for shaft 152. The top of neck 110 serves as a stop point for brush 150. The length of neck 110 is selected so as to conveniently place brush 150 at the back of the mouth and avoid the need to put the user's hand in his or her mouth.

In some embodiments, membrane 158 is located in coupler 157, or at or near the top of neck 110 to prevent liquid leaking into the shaft channel. Membrane 158 is a flexible toroidal surface that enables shaft 152 to move up and down through its center.

In other embodiments, the bottom of brush 150 has a dish-shaped portion (not shown) that abuts the top of neck 110. When retracted, the dish-shaped portion fits snugly in the channel for brush 150 and prevents leakage into the channel.

Handle 120 provides a comfortable area for a user's hand to wrap around. The top of handle 120 is formed into cavity 165. Cavity 165 has opposing slots 124, discussed below. On the outside of handle 120, slots 124 are formed in respective U-shaped grooves 122. The bottom of handle 120 is connected to base 162. Base 162, at the bottom of handle 120, generally rests in the user's palm, and so has a comfortable rounded shape lacking sharp edges that would cause discomfort to a user.

Figures 7A, 7B, 7C:
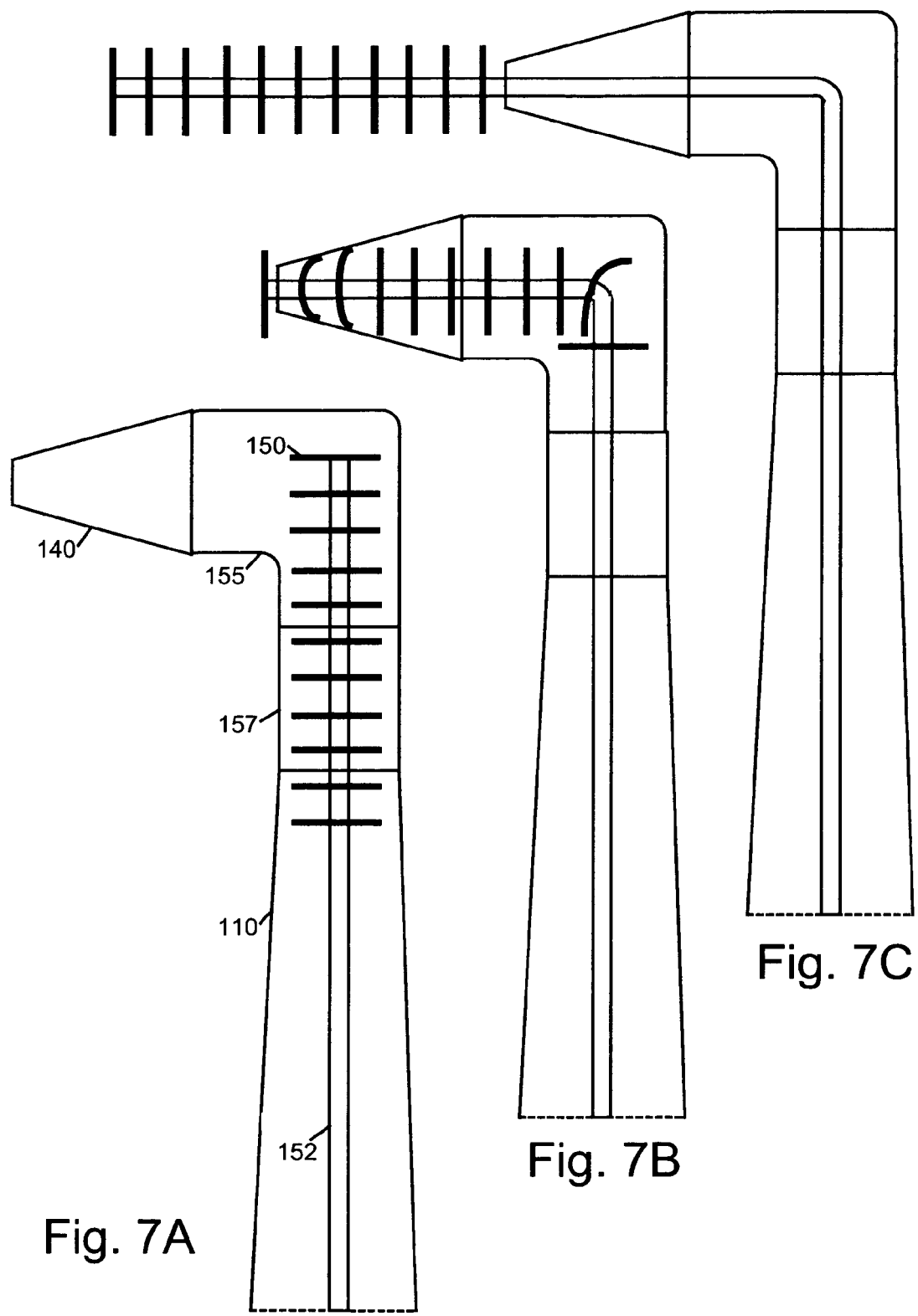
FIGS. 7A, 7B, 7C are views of interproximal cleaning device 100 in retracted, intermediate retracted/extended and extended configurations.

Brush 150 comprises nylon bristles attached to shaft 152. The length of the bristles may depend on the use, i.e., for teeth or implants and the size of the interproximal space. Generally, the bristle diameter is 1.5-8.5 mm, while shaft 152 has a diameter of 0.4-1.3 mm; the bristles have a length of 11-22 mm. When brush 150 is completely retracted or completely extended, it has a linear shape; at intermediate retraction points, brush 150 may be curved. FIG. 7A shows brush 150 in a completely retracted configuration, FIG. 7B shows brush 150 in an intermediate retracted/extended configuration, and FIG. 7C shows brush 150 in a completely extended configuration. In FIG. 2, brush 150 has a cylindrical shape with uniform cross-section. In other embodiments, brush 150 is tapered at its point to better fit into small interproximal embrasures. In still other embodiments, brush 150 is of generally conical shape and includes elastomeric flat-faced flanges extending perpendicularly outwards from the base to the tip in a staggered pattern. Other brush shapes and compositions will be apparent to those of ordinary skill.

Shaft 152 is formed of flexible material that returns to its original shape after being deformed, such as nickel-titanium. In some embodiments, the top part of shaft 152 is coated with plastic or silicone or brush 150 and shaft 152 are made out flexible plastic with plastic bristles to ensure that it does not scratch tooth surfaces or implant posts. The top part of shaft 152 is formed of twisted wire that restrains bristles; in other embodiments, the top of shaft 152 is otherwise suitably connected to brush 150. Shaft 152 is enclosed along most of its length by elbow 155, coupler 157 and neck 110, which together have an internal channel (not shown) formed by guide pieces or a hollowing. The bottom of shaft 152 is enclosed by coil 160. In the embodiment of FIG. 2, the bottom of shaft 152 is connected to the bottom of coil 160. In other embodiments, the bottom of shaft 152 is connected to a circular plate having a diameter larger than the diameter of coil 160. In some embodiments, the bottom of shaft 152 is connected to the top of coil 160.

Coil 160 is a spiral of metal formed into a spring. In other embodiments, coil 160 is formed of plastic. In other embodiments, coil 160 is omitted. Coil 160 serves to exert pressure against the bottom of shaft 152 and facilitate retraction of shaft 152. The top of coil 160 fits into the underside of neck 110. In some embodiments, neck 110 has a cavity at its base for accommodating the top of coil 160. The bottom of coil 160 fits into cavity 165 at the top of handle 120.

Controller 130 is formed by snapping together surfaces 130A and 130B, each of which is formed of plastic or metal and preferably has ridges to increase traction with respect to the user's thumb. The underside of surface 130A has prong 131A projecting perpendicularly therefrom, while the underside of surface 130B has prong receiver 131B projecting perpendicularly therefrom. Prong 131A snaps into prong receiver 131B. The top of surfaces 130A, 130B move along landing pads 132 formed on opposite sides in the base of neck 110 (only one landing pad 132 is visible in FIG. 2). The bottom of surfaces 130A, 130B move along U-shaped grooves 122 formed on opposite sides in the top of handle 120 (only one U-shaped groove 122 is visible in FIG. 2). U-shaped groove 122 has slots 124 for accommodating prong 131A and prong receiver 131B.

Figure 3:
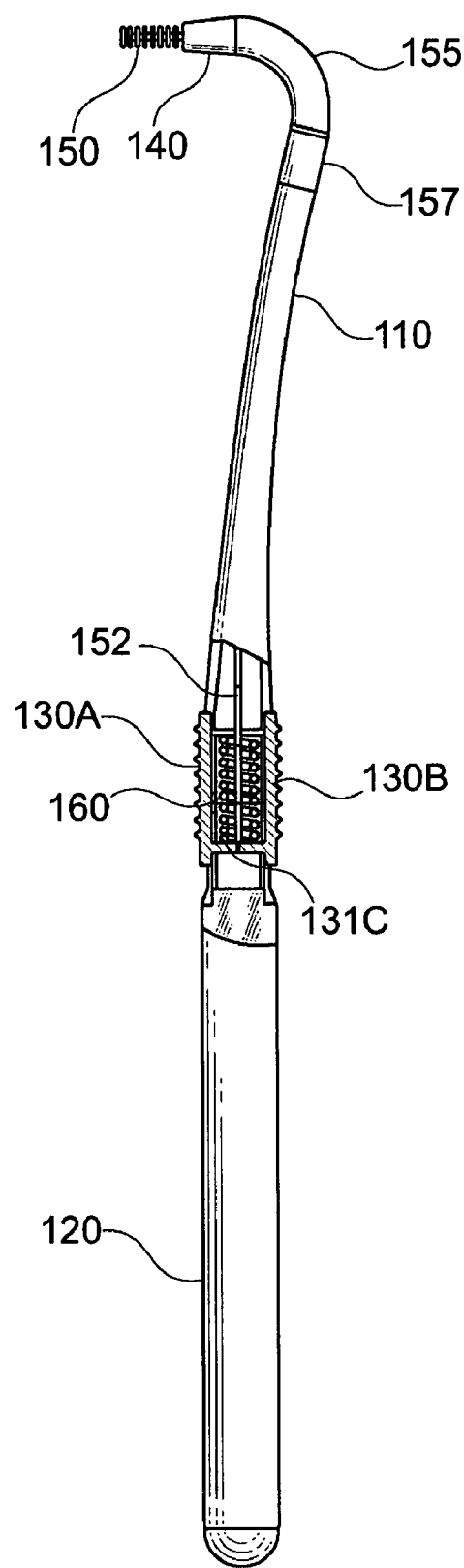
FIG. 3 is a partially cut-away side view of interproximal cleaning device 100.
Figure 6A:
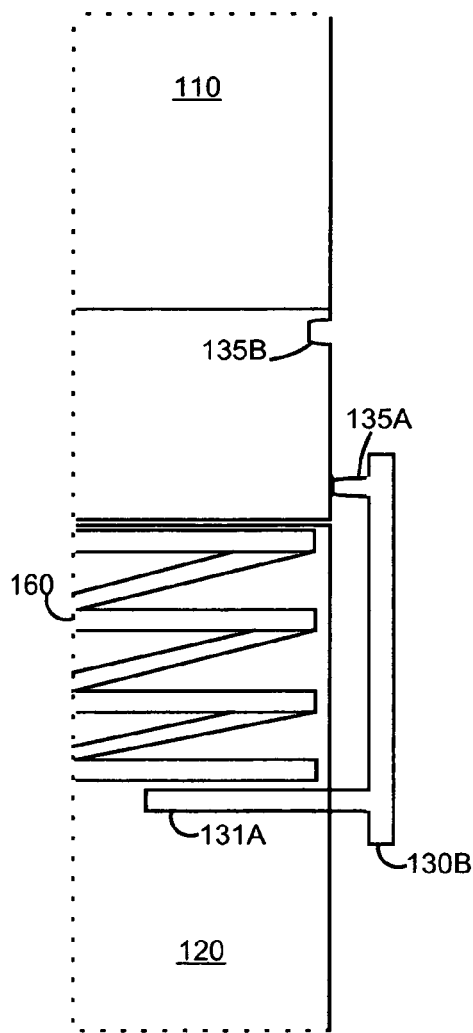
FIGS. 6A and 6B are views of internal hook 135 of interproximal cleaning device 100.
Figure 6B:
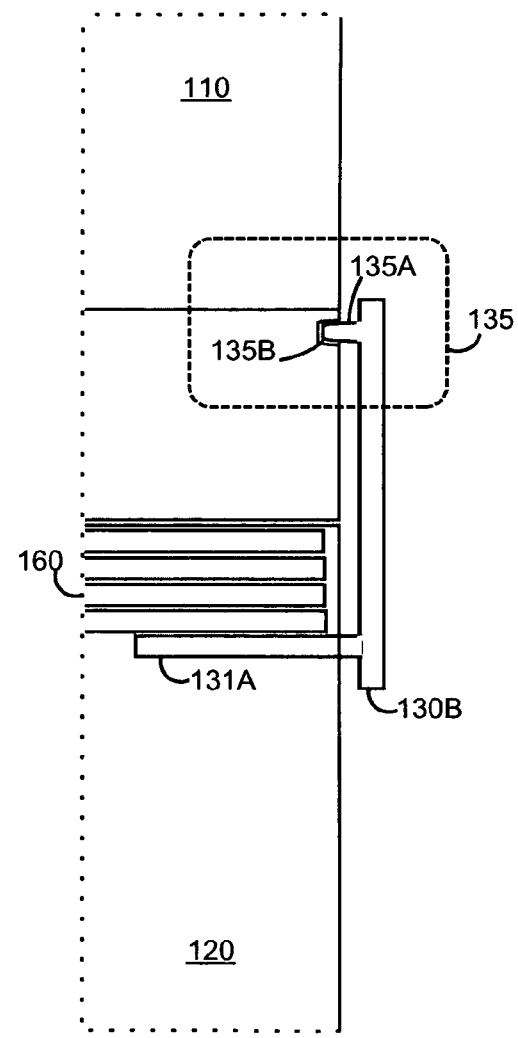

As shown in FIG. 3, prong 131A is snapped into prong receiver 131B to form member 131C, so that coil 160 rests atop member 131C. Pushing controller 130 to its topmost position in landing pad 132 compresses coil 160 providing energy thereto, and fully extends brush 150. Pushing controller 130 to its bottommost position in U-shaped groove 122 enables coil 160 to return to its natural length using its stored energy to pull shaft 152 downwards, and fully retracts brush 150. In operation, a user's thumb moves controller 130 up and down, to cause brush 150 to move in front-to-back and back-to-front paths along the interproximal surfaces of adjacent teeth. Thus, device 100 can remain generally stationary while brush 150 is at the back of a user's mouth and the user's thumb is controlling the movement of brush 150. This configuration is convenient. Additionally, for persons with impaired gripping ability, such as those with arthritis, it is substantially easier to hold handle 120 and move controller 130, than to move a thinner conventional device at the back of the mouth. In some embodiments, there is a structure, such as internal hook 135, for fixing controller 130 in its topmost position, thereby causing interproximal device 160 to function with a non-retractable brush. FIG. 6A shows internal hook 135 in its normal unused position. FIG. 6B shows internal hook 135 in use; hook 135A locks into depression 135B.

Dimensions of the parts of device 100 may be as follows. These dimensions may vary depending on the particular construction of device 100, and its intended user, such as adult or child.

Lengths: tip 140—5 mm; brush 150—11-22 mm; elbow 155 (including curvature)—10-12 mm; coupler 157—5 mm; neck 110—59-61 mm; coil 160—10 mm; surface 130A, 130B—26 mm; and handle 120—100 mm. The length of landing pad 132 depends on the length of brush 150, with a longer lading pad length corresponding to a longer brush length. The inner circumference of tip 140 is about 0.5-1.5 mm.

Figure 4:
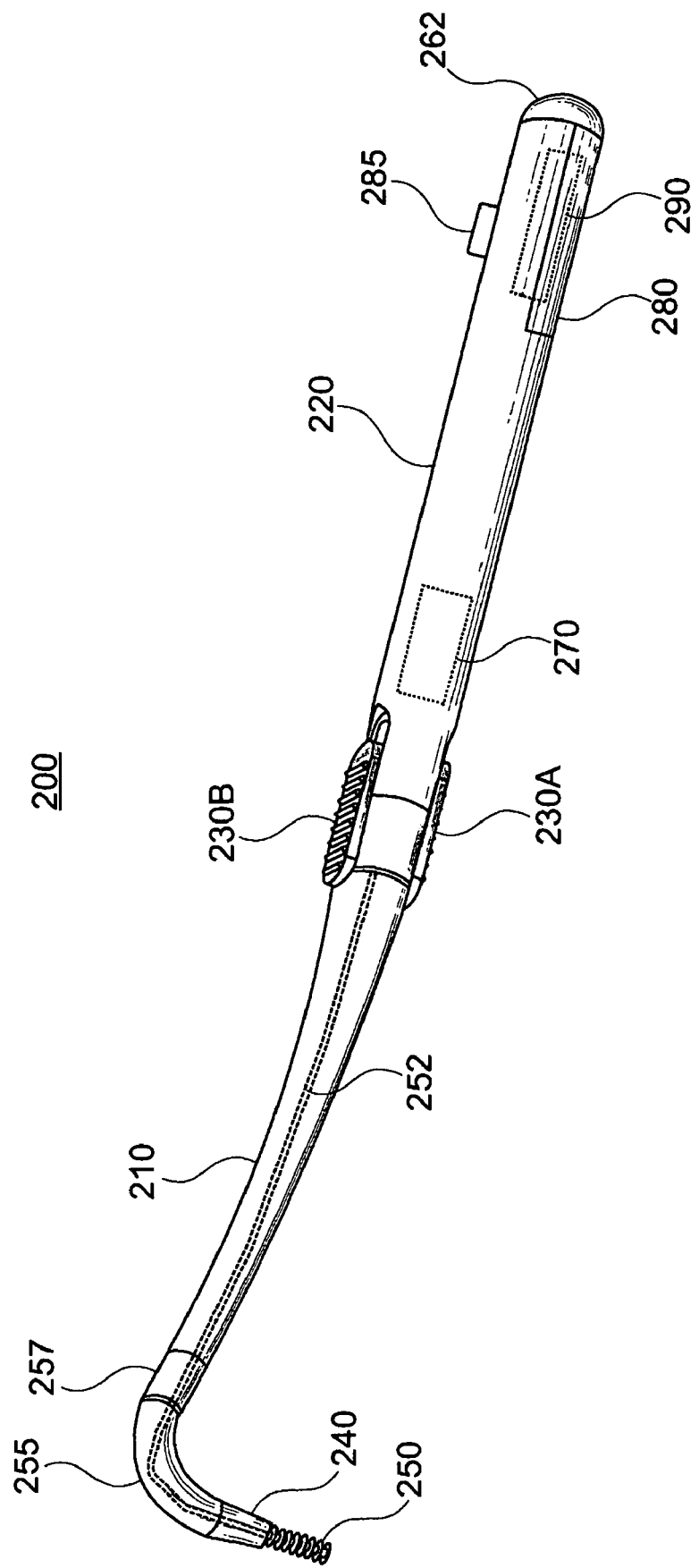
FIG. 4 is a three-dimensional view of interproximal cleaning device 200.

FIG. 4 is a three-dimensional view of interproximal cleaning device 200 that is similar to interproximal cleaning device 100; for brevity, only the differences are discussed.

U.S. Pat. No. 5,123,841 (Millner), the disclosure of which is hereby incorporated by reference in its entirety, shows an interproximal dental plaque remover having a substantially fixed brush that is vibrated by a motor with an eccentrically mounted cylindrical weight. The vibration splays the bristles of the brush into the furca (below gum line), subgingival pockets at the cemento-enamel junction (CEJ), thereby disrupting adherent plaque colonies and mobilizing bacteria into the subgingival fluids.

Interproximal cleaning device 200 includes motor 270, battery cover 280, battery 290 and activation switch 285. Motor 270 operates as described in the Millner '841 patent by imparting vibratory motion to shaft 252 so that, in addition to the in-and-out manual movement of brush 250, there is also small vibratory movement. Battery cover 280 enables access to a chamber for holding battery 290. Activation switch 285 enables a user to activate and deactivate motor 270. Accordingly, device 200 can be used in three modes: (a) with motor 270 deactivated, so that device 200 operates exactly as does device 100, (b) with motor 270 activated and brush 250 maximally extended, so that device 200 operates substantially as described in the Millner '841 patent, or (c) with motor 270 activated and brush 250 being manually moved between extension and retraction.

Figure 5:
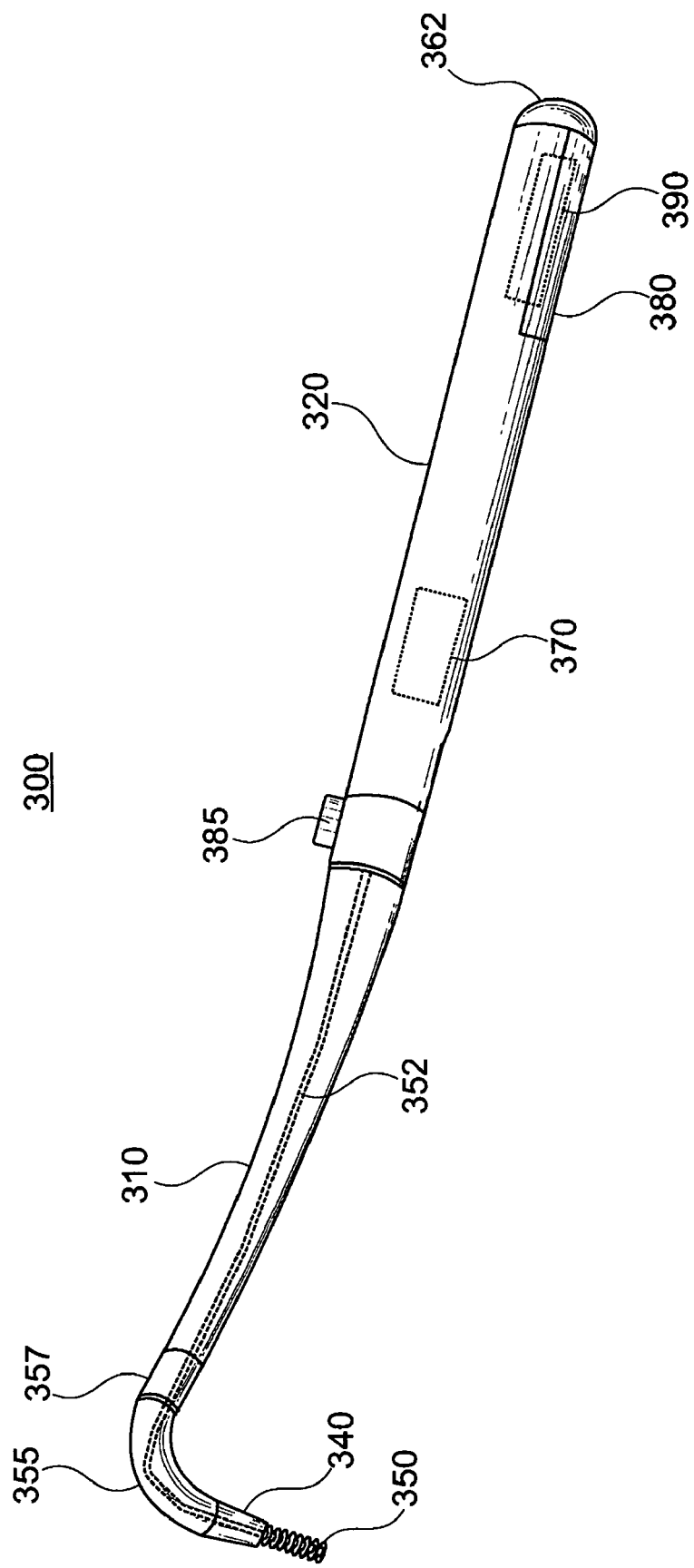
FIG. 5 is a three-dimensional view of interproximal cleaning device 300.

FIG. 5 is a three-dimensional view of interproximal cleaning device 300 that is similar to interproximal cleaning device 200; for brevity, only the differences are discussed.

U.S. Pat. No. 4,787,847 (Martin), the disclosure of which is hereby incorporated by reference in its entirety, shows an electric toothbrush wherein the brush is vibrated at subsonic frequencies to assist in subgingival plaque removal.

Interproximal cleaning device 300 includes motor 370 substantially as described in Martin, except that device 300 is configured so that motor 370 causes brush 350 to extend and retract at generally subsonic frequencies. Device 300 is powered by battery 390 rather than by a connection to a wall outlet. Device 300 lacks the ability for finger-operated manual retraction and extension of brush 350; however, manual movement of brush 350 can be accomplished by moving handle 320. Activation switch 385 is preferably located between neck 310 and handle 320, i.e., at the bottom of neck 310 and/or the top of handle 320, so that the user can more easily activate and deactivate motor 370 while using device 300. Generally, device 300 serves as an interproximal powered tooth brush.

Although illustrative embodiments of the present invention, and various modifications thereof, have been described in detail herein with reference to the accompanying drawings, it is to be understood that the invention is not limited to these precise embodiments and the described modifications, and that various changes and further modifications may be effected therein by one skilled in the art without departing from the scope or spirit of the invention as defined in the appended claims.

What is claimed is:

1. A device for interproximal cleaning, comprising:
a brush,
a shaft connected to the brush,
a neck surrounding the shaft along a substantial portion of the length of the shaft,
an elbow attached to the neck and surrounding the shaft, the elbow having a curvature that is adjustable to a desired position according to a preference of a user,
a tip having a generally conical tapered shape and a hollow interior, located at the end of the elbow opposite the neck and surrounding the shaft, the tip for positioning the device so that the brush is perpendicular to the teeth, and
a controller coupled to the shaft at the end of the shaft opposite the brush, the controller being mounted at the base of the neck so as to be movable between a first position that extends the brush away from the neck, and a second position that retracts the brush towards the neck, with the brush passing through the hollow interior of the tip as the brush is extended and retracted so that the brush is cleaned by a squeegee action each time it is retracted.

2. The device of claim 1, wherein the brush has nylon bristles attached to the shaft.

3. The device of claim 1, wherein the shaft is formed of a material that returns to its original shape after being deformed.

4. The device of claim 3, wherein the material is nickel-titanium.

5. The device of claim 1, wherein the controller has at least one surface for manual operation thereof.

6. The device of claim 1, further comprising a motor for moving the shaft so that the brush extends and retracts.

7. The device of claim 1, further comprising a motor for vibrating the shaft.

8. The device of claim 1, further comprising a membrane having a flexible toroidal surface located at the top of the neck to serve as a barrier against liquid.

9. The device of claim 1, wherein the tip is removably attached to the elbow.

10. The device of claim 1, further comprising means for locking the controller in the first position.

11. The device of claim 1, further comprising a spring located at the base of the shaft, the spring being in an uncompressed state when the controller is in the second position and being in a compressed state when the controller is in the first position.

* * * * *